United States Patent
James

(10) Patent No.: US 8,768,478 B1
(45) Date of Patent: Jul. 1, 2014

(54) SIGNAL EVALUATION IN BINAURAL AND HYBRID HEARING PROSTHESIS CONFIGURATIONS

(71) Applicant: Christopher John James, Toulouse (FR)

(72) Inventor: Christopher John James, Toulouse (FR)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/755,171

(22) Filed: Jan. 31, 2013

(51) Int. Cl.
*A61N 1/36* (2006.01)

(52) U.S. Cl.
USPC .......................................... 607/57

(58) Field of Classification Search
USPC .......................................... 607/57
See application file for complete search history.

(56) References Cited

U.S. PATENT DOCUMENTS

2011/0125218 A1    5/2011    Busby

OTHER PUBLICATIONS

E. Gaudrain & R. P. Carlyon, Using Zebra-speech to study sequential and simultaneous speech segregation in a cochlear-implant simulation, J. Acoust. Soc. Am., vol. 133, No. 1, pp. 502-518, Cambridge, UK (Jan. 2013).

*Primary Examiner* — George Manuel
(74) *Attorney, Agent, or Firm* — McDonnell Boehnen Hulbert & Berghoff LLP

(57) ABSTRACT

The present application discloses systems and methods to address situations in a binaural hearing prosthesis configuration in which each hearing prosthesis receives audio signals that have differing audio signal measures (e.g., signal to noise ratios (SNRs)). In accordance with one embodiment, a method is provided and includes receiving a first audio signal from a first transducer, receiving a second audio signal from a second transducer, evaluating the first audio signal and determining thereby a first audio signal measure, evaluating the second audio signal and determining thereby a second audio signal measure, based on the evaluating, identifying from among the first audio signal and the second audio signal a particular audio signal that has a certain quality with respect to the audio signal measures (e.g., the highest SNR), and applying stimulation to a recipient in accordance with the identified audio signal.

19 Claims, 6 Drawing Sheets

Article of Manufacture 900

Program Instructions 902

- receiving a first signal via a first receiver

- receiving a second signal via a second receiver

- determining a signal-to-noise ratio (SNR) of the first signal and determining an SNR of the second signal

- identifying from among the first signal and the second signal a particular signal that has a highest SNR

- causing one or both of the first stimulation prosthesis and the second stimulation prosthesis to apply stimulation to an implant recipient in accordance with at least part of the identified signal Computer Readable Medium 903

Computer Recordable Medium 904

Fig. 9

SIGNAL EVALUATION IN BINAURAL AND HYBRID HEARING PROSTHESIS CONFIGURATIONS

BACKGROUND

Various types of hearing prostheses may provide persons with different types of hearing loss with the ability to perceive sound. Hearing loss may be conductive, sensorineural, or some combination of both conductive and sensorineural hearing loss. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sounds into the person's ear. Vibration-based hearing devices typically include a small microphone to detect sound, and a vibration mechanism to apply vibrations corresponding to the detected sound to a person's bone, thereby causing vibrations in the person's inner ear, thus bypassing the person's auditory canal and middle ear. Vibration-based hearing devices may include bone conduction hearing devices, direct acoustic cochlear implants, or other vibration-based devices. A bone conduction hearing device typically utilizes a surgically-implanted mechanism to transmit sound via direct vibrations of the skull. Similarly, a direct acoustic cochlear implant typically utilizes a surgically-implanted mechanism to transmit sound via vibrations corresponding to sound waves to generate fluid motion in a person's inner ear. Other non-surgical vibration-based hearing devices may use similar vibration mechanisms to transmit sound via direct vibration of teeth or other cranial or facial bones.

Persons with certain forms of sensorineural hearing loss may benefit from cochlear implants and/or auditory brainstem implants. For example, cochlear implants may provide a person having sensorineural hearing loss with the ability to perceive sound by stimulating the person's auditory nerve via an array of electrodes implanted in the person's cochlea. The cochlear implant detects sound waves and converts them into a series of electrical stimulation signals that are delivered to the implant recipient's cochlea via the array of electrodes. Auditory brainstem implants may use technology similar to cochlear implants, but instead of applying electrical stimulation to a person's cochlea, auditory brainstem implants apply electrical stimulation directly to a person's brain stem, bypassing the cochlea altogether. Electrically stimulating auditory nerves in a cochlea with a cochlear implant or electrically stimulating a brainstem may enable persons with sensorineural hearing loss to perceive sound. It is also possible to stimulate in a hybrid fashion in the same ear such that acoustic amplification can be used to stimulate mildly-to-severely impaired hearing frequencies, while at the same time the cochlear implant stimulates the remaining severely-to-profoundly impaired frequencies. This configuration constitutes a "hybrid" implant device.

Persons with varying degrees of either type of hearing loss may benefit from a binaural or hybrid hearing prosthesis configuration. For example, a person with conductive hearing loss in the left ear and sensorineural hearing loss in the right ear may benefit from a binaural hearing prosthesis configuration in which an acoustic hearing aid is positioned in the left ear and a cochlear implant is implanted in the right ear. Moreover, a person with different degrees and/or types of hearing loss depending upon sound frequency in the same ear may benefit from a hybrid hearing prosthesis configuration in which a cochlear implant and another type of hearing prosthesis (such as an acoustic actuator or hearing-aid receiver) are positioned in the same ear, and another hearing prosthesis in the other ear.

SUMMARY

The present application discloses systems and methods to address situations in a binaural hearing prosthesis configuration in which each hearing prosthesis receives audio signals that have differing audio signal measures (e.g., signal to noise ratios (SNRs)). In accordance with at least some embodiments of the present disclosure, a method is provided and includes receiving a first audio signal from a first transducer, receiving a second audio signal from a second transducer, evaluating the first audio signal and determining thereby a first audio signal measure, evaluating the second audio signal and determining thereby a second audio signal measure, based on the evaluating, identifying from among the first audio signal and the second audio signal a particular audio signal that has a certain quality with respect to the audio signal measures (e.g., a highest SNR), and applying stimulation to an implant recipient in accordance with the identified audio signal.

In accordance with another embodiment, another method is provided and includes receiving an audio signal from a transducer, dividing the audio signal into a first segment and a second segment, the first segment comprising parts of the audio signal that are in frequency bands of greater magnitude than a threshold frequency, and the second segment comprising parts of the audio signal that are in frequency bands of smaller magnitude than the threshold frequency, transmitting the first segment to a first hearing prosthesis, and transmitting the second segment to a second hearing prosthesis.

In accordance with another embodiment, a system is provided and includes a first stimulation prosthesis, a second stimulation prosthesis, and coupled to at least one of the first stimulation prosthesis and the second stimulation prosthesis, one or more processors configured for (i) receiving a first signal via a first receiver, (ii) receiving a second signal via a second receiver, (iii) determining an audio signal measure of the first signal and determining an audio signal measure of the second signal, (iv) identifying from among the first signal and the second signal a particular signal that has a certain quality with respect to the audio signal measures (e.g., a highest SNR), and (v) causing one or both of the first stimulation prosthesis and the second stimulation prosthesis to apply stimulation to an implant recipient in accordance with at least part of the identified signal.

BRIEF DESCRIPTION OF THE DRAWINGS

FIG. 9 shows an example of an article of manufacture including computer readable media with instructions for executing functions, according to an example embodiment.

DETAILED DESCRIPTION

The following detailed description describes various features and functions of the disclosed systems and methods with reference to the accompanying figures. In the figures, similar symbols typically identify similar components, unless context dictates otherwise. The illustrative system and method embodiments described herein are not meant to be limiting. Certain aspects of the disclosed systems and methods can be arranged and combined in a wide variety of different configurations, all of which are contemplated herein.

Certain aspects of the disclosed systems, methods, and articles of manufacture may be described herein with reference to hearing prosthesis embodiments and more particularly cochlear implant embodiments. However, the disclosed systems, methods, and articles of manufacture are not so limited. Many of the disclosed features and functions described with respect to the cochlear implant embodiments may be equally applicable to other embodiments that may include other types of medial stimulation prostheses including, prosthetic-limb stimulation devices, vibration-based hearing devices, direct acoustic cochlear implants, auditory brain stem implants, or any other type of medical stimulation prosthesis that is configured such that one component generates commands and transmits the commands across a data link to another component, which applies or executes the commands.

Figure 2:
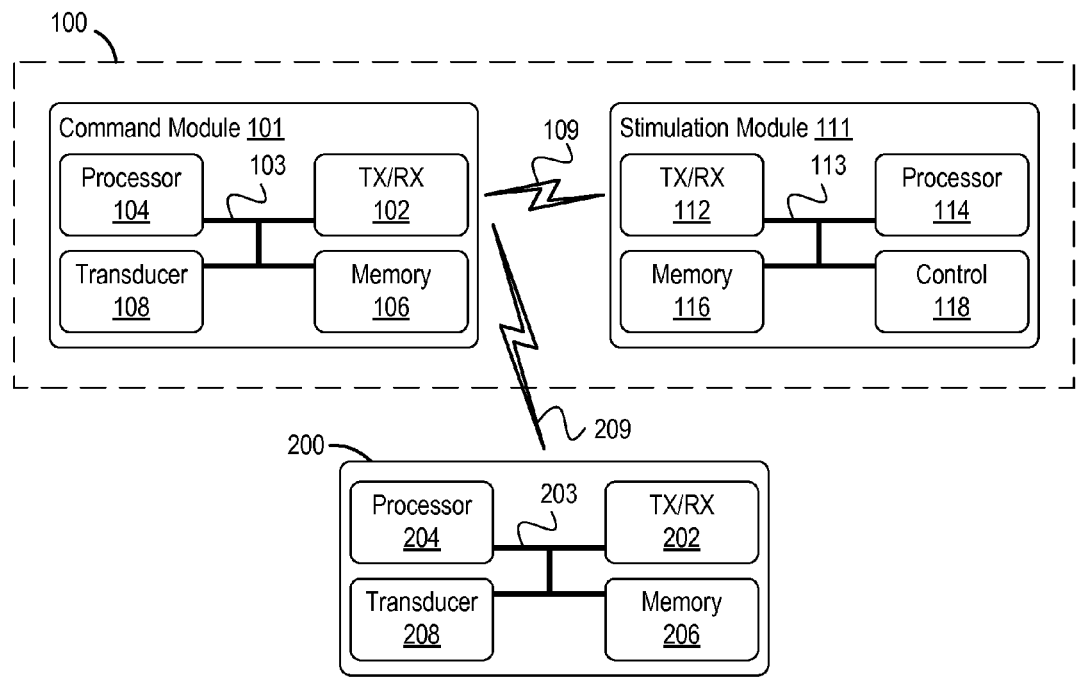
FIG. 2 shows a block diagram of certain selected hearing prosthesis components according to some embodiments of the disclosed systems and methods.

As a general matter, in some binaural hearing prosthesis configurations, such as the one depicted in FIG. 2, the transducer associated with one hearing prosthesis is typically located near or otherwise configured to affect one outer ear, middle ear and/or inner ear, whereas the transducer associated with the other hearing prosthesis is typically located near or otherwise configured to affect the other outer ear, middle ear and/or inner ear. In some situations, such an arrangement leads to audio signals received at each hearing prosthesis that have differing audio signal measures (e.g., signal-to-noise-ratios (SNRs)). One example of such a situation typically occurs when speech or other sounds of interest originate from one side of the recipient's head, rather than in front of or behind the recipient. The recipient's head may cause significant attenuation of sound waves of all frequencies, but particularly in sound waves of 1 kHz and above. As a result, the transducer located on the side of the head opposite to the origin of the sound often receives a signal with a lower SNR than the signal received by the transducer located on the other side of the head. This can lead to a poor recipient experience.

In addition, different types of hearing prostheses tend to be differently suited for handling certain types of sounds. For instance, on the one hand cochlear implants tend to be well-suited for speech recognition because they are well-suited for providing stimulation in response to higher-frequency sound waves. On the other hand, acoustic hearing devices (e.g., traditional hearing aids, bone conduction devices, middle ear implants, etc.) tend to be well-suited for speech quality because they are well-suited for providing stimulation in response to lower-frequency sound waves. Therefore, in a binaural or hybrid hearing prosthesis configuration in which one of the two hearing prostheses is a cochlear implant, for instance, some high-frequency sound waves may be attenuated before they reach the cochlear implant's transducer. Thus, as a result, the sound experienced by the implant recipient may be less than desirable. Therefore, to address these situations, and perhaps others, provided herein are processes and corresponding systems in which audio signals received at each hearing prosthesis are evaluated, and from among them, a signal with a certain quality with respect to an audio signal measure (e.g., a highest SNR, a highest input speech level, etc.) is identified and transmitted to each hearing prosthesis for use in applying stimulation to the prosthesis recipient.

Example Hearing Prosthesis Configurations

Figure 1:
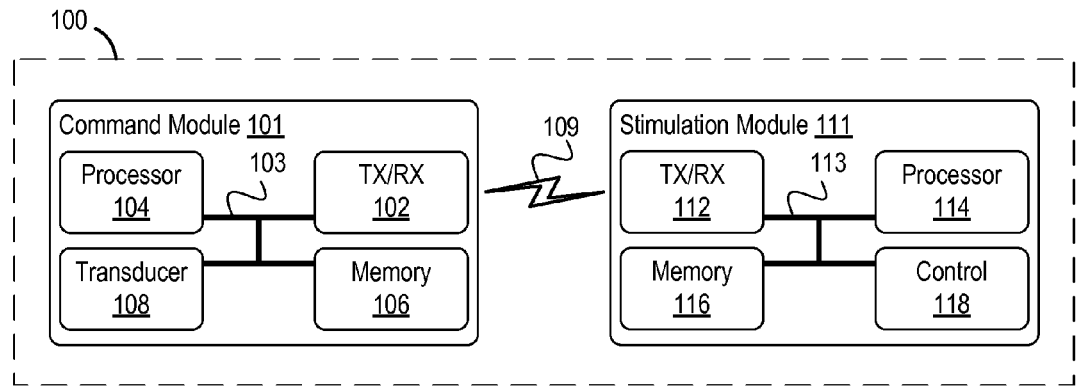
FIG. 1 shows a block diagram of certain selected hearing prosthesis components according to some embodiments of the disclosed systems and methods.

FIG. 1 shows a block diagram of an example hearing prosthesis 100 according to some embodiments of the disclosed systems and methods. In some embodiments, hearing prosthesis 100 is a cochlear implant; however, in other embodiments, hearing prosthesis 100 is another kind of implant, such as a vibration-based hearing device, a direct acoustic cochlear implant, or an auditory brain stem implant. The hearing prosthesis shown in FIG. 1 may be implanted into a hearing prosthesis recipient according to any general implant procedure. In some embodiments, hearing prostheses, such as hearing prosthesis 100, have additional or different components than those depicted in FIG. 1; but, for brevity's sake, the configuration depicted in FIG. 1 focuses on a selected set of components that may be helpful to illustrate certain aspects of the disclosed embodiments.

In the embodiment shown in FIG. 1, hearing prosthesis 100 includes a command module 101 and a stimulation module 111. Although not shown in FIG. 1, in some embodiments, the command module 100 is included within an external component assembly that is directly or indirectly attached to the body of the hearing prosthesis recipient, whereas the stimulation module 111 is included within an internal component assembly that is temporarily or permanently implanted in the hearing prosthesis recipient. However, in other embodiments, the command module 100 and the stimulation module 111 are both included within one or more internal component assemblies, each of which are temporarily or permanently implanted in the hearing prosthesis recipient.

The command module 101 includes a transmit/receive sub-module 102, a processor sub-module 104, a memory sub-module 106, and a transducer sub-module 108, all of which may be connected directly or indirectly via circuitry 103. Similarly, the stimulation module 111 includes a transmit/receive sub-module 112, a processor sub-module 114, a memory sub-module 116, and a control sub-module 118, all of which may be connected directly or indirectly via circuitry 113. In some embodiments, the sub-modules of the command module 101 are located on a single integrated circuit, whereas in other embodiments, the sub-modules of the command module 101 are spread out across two or more integrated circuits. Likewise, in some embodiments, the sub-modules of the stimulation module 111 are located on a single integrated circuit, whereas in other embodiments, the sub-modules of the stimulation module are spread out across two or more integrated circuits.

In the embodiment shown in FIG. 1, transducer 108 is configured to detect sound waves and generate an audio signal representative of those sound waves. Transducer 108 may be further configured to transmit to processor 104, via circuitry 103, a generated audio signal that is based on the detected sound waves. Depending on the desired configuration, transducer 108 may be one or more microphones, one or more telecoil induction pickup coils, or some other sound-detection device now known or later developed.

In the embodiment shown in FIG. 1, processor 104 is configured to receive, analyze, and encode an audio signal sent from transducer 108 (or another source) into one or more stimulation commands according to a particular sound-coding strategy. Depending on the desired configuration, processor 104 may include one or more processors, including but not limited to, programmable processors, application specific integrated circuits, programmable logic arrays, digital signal processors, and/or other general and/or special purpose processors configured to perform one or more of the functions of the hearing prosthesis 100 as described further below.

In the embodiment shown in FIG. 1, the transmit/receive sub-module 102 is configured to transmit stimulation commands produced by processor 104 to the stimulation module 111. In addition, the transmit/receive sub-module 102 is also configured to send other transmissions to the stimulation module 111, such as instructions to carry out one or more hearing prosthesis diagnostic tests, or any other type of transmission. Such transmission is carried out by way of data link 109 and may be of any protocol or format. In some embodiments, transmit/receive sub-module 102 includes a coil of a transcutaneous energy transfer system along with associated circuitry to drive the coil. However, in other embodiments, transmit/receive module 102 may be any radio-frequency (RF) interface or other wired or wireless communication interface that facilitates data communications.

As a general matter, data link 109 may be any coupling that enables data transmission between the transmit/receive sub-module 102 and the transmit/receive module 112. In some embodiments, data link 109 is a transcutaneous RF inductive link. In other embodiments, data link 109 is any air interface or other wired connection. Typically, data link 109 is a half-duplex data link. A half-duplex data link is a data link across which the command module 101 and the stimulation module 111 do not simultaneously transmit packets. Although, in other embodiments, data link 109 is a full-duplex data link. A full-duplex data link is a data link across which the command module 101 and the stimulation module 111 may simultaneously transmit packets.

In the embodiment shown in FIG. 1, memory module 106 includes one or more computer-readable storage media that can be read from, written to, or otherwise accessed by processor 104. Moreover, the storage media of memory 106 is also configured to be read from, written to, or otherwise accessed by one or more of the transmit/receive sub-module 102 and/or the transducer 108. In some embodiments, the storage media in the memory sub-module 106 is configured to store configuration data for the hearing prosthesis 100 or other programming instructions that facilitate general operation of the hearing prosthesis 100 in accordance with the functions described herein.

The hearing prosthesis 100 shown in FIG. 1 also includes a stimulation module 111, which generally includes functionality similar to that of the command module 101. For instance, stimulation module 111 includes a transmit/receive sub-module 112, which includes functionality similar to that of transmit/receive sub-module 102. In some embodiments, the transmit/receive sub-module 112 may be configured to receive over the data link 109 stimulation commands or other types of data transmitted by command module 101. Depending on the configuration, the transmit/receive sub-module 112 may be the counterpart of transmit/receive sub-module 102 insofar as transmit/receive sub-module 112 may include an internal coil of the noted transcutaneous energy transfer system. In some embodiments, however, transmit/receive sub-module 112 may be any RF interface or other wired or wireless communication interface that facilitates data communications.

Similar to processor 104, processor 114 may include one or more processors, including but not limited to, programmable processors, application specific integrated circuits, programmable logic arrays, digital signal processors, and/or other general and/or special purpose processors configured to perform one or more of the functions of the hearing prosthesis 100, such as operating control sub-module 118, as described further below.

In general, the arrangement of transmit/receive sub-modules 102 and 112, as depicted in this embodiment, operates to exchange messages between processor 104 and processor 114. In addition, this arrangement operates to exchange messages between a fitting system (not shown) and processor 114 via processor 104. In other embodiments, other arrangements are possible as well.

Similar to memory sub-module 106, memory sub-module 116 may include one or more computer-readable storage media that can be read from, written to, or otherwise accessed by processor 114. In some embodiments, the storage media of the memory module 106 may also be read from, written to, or otherwise accessed by a fitting system. Additionally, the storage media of memory 106 may also be read from, written to, or otherwise accessed by one or more of the transmit/receive sub-module 112 and/or the control sub-module 118. In some embodiments, the storage media in the memory sub-module 116 may be configured to store configuration, or MAP, data for the hearing prosthesis 100 or other programming instructions that facilitate general operation of the hearing prosthesis 100 in accordance with the functions described herein. The storage media of the memory sub-module 116 may also be configured to store the results of one or more diagnostic tests that are initiated, performed, or otherwise controlled in whole or in part by either processor 114, control sub-module 118, or a fitting system.

Depending on the embodiment, hearing prosthesis 100 may include additional components that are not shown in FIG. 1. For example, in embodiments in which hearing prosthesis 100 is a cochlear implant, the cochlear implant may include an array of two or more electrodes. Typically, the electrodes are positioned along the recipient's cochlea. During operation, the stimulation module 111, in response to receiving one or more stimulation commands from the command module 100, applies via control sub-module 118 one or more electrical signals to the electrode array in order to stimulate the recipient's cochlea. However, as indicated above, depending on the embodiment, an electrode array, or other similar stimulation apparatus, may be positioned along other portions of the recipient, including for example the outer ear, inner ear, middle ear, cranial or facial bones, teeth, or brain stem.

Depending on the embodiment, control sub-module 118 includes circuitry configured to control and manage the electrode array or other similar stimulation apparatus. By way of example, such circuitry may include a signal generation sub-module, a transmit amplifier sub-module, a switching sub-module, a receive amplifier sub-module, and/or a signal measurement sub-module (not shown).

FIG. 2 depicts an example binaural hearing prosthesis arrangement that includes hearing prosthesis 100 and another hearing prosthesis 200. In accordance with one embodiment, hearing prosthesis 100 is a cochlear implant and hearing prosthesis 200 is another type of device, such as an acoustic hearing aid or a bone conduction device. Such an arrangement is typically beneficial in cases in which the prosthesis recipient has some form of hearing loss in each ear. For example, in some embodiments, the cochlear implant is implanted in an ear with total hearing loss, whereas an acoustic hearing aid is used on an ear with less than total hearing loss. In other embodiments, the combination of hearing prosthesis 100 and hearing prosthesis 200 is referred to as a hybrid hearing prosthesis and is implanted or positioned in one ear. In other embodiments, other arrangements are possible as well, including for example two cochlear implants, two acoustic hearing aids, two bone conduction devices, two hybrid electric-acoustic devices or any combination of these or other types of devices.

As depicted in FIG. 2, hearing prosthesis 200 includes components similar to those described above with respect to command module 101 of hearing prosthesis 100. For instance, hearing prosthesis 200 includes a transmit/receive sub-module 202, which includes functionality similar to that of transmit/receive sub-module 102 of command module 101. In the embodiment depicted, hearing prosthesis 200 is configured to communicate with hearing prosthesis 100 (and more particularly, with command module 101) by utilizing the transmit/receive sub-module 202 and data link 209. In accordance with the features and functionality described further herein, hearing prosthesis 200 and hearing prosthesis 100 communicate certain signals and instructions across data link 209. Generally, data link 209 is any RF interface or other wired or wireless communication interface that facilitates data communications.

Similar to processor 104, processor 204 may include one or more processors, including but not limited to, programmable processors, application specific integrated circuits, programmable logic arrays, digital signal processors, and/or other general and/or special purpose processors configured to perform one or more of the functions of the hearing prosthesis 200. In general, the arrangement of transmit/receive sub-modules 102 and 202, as depicted in this embodiment, operates to exchange messages between processor 204 and processor 104. In other embodiments, other arrangements are possible as well.

Similar to memory sub-module 106, memory sub-module 206 may include one or more computer-readable storage media that can be read from, written to, or otherwise accessed by processor 204. In some embodiments, the storage media of memory 206 may also be read from, written to, or otherwise accessed by other entities.

Similar to transducer 108, transducer 208 is generally configured to detect sound waves and generate an audio signal representative of those sound waves. In embodiments in which hearing prosthesis 100 is implanted or positioned in one ear of a prosthesis recipient and hearing prosthesis 200 is implanted or positioned in the other ear of the recipient, transducer 108 is positioned at the ear in which hearing prosthesis 100 is located and transducer 208 is positioned at the ear in which hearing prosthesis 200 is located. However, in other embodiments in which hearing prosthesis 100 and hearing prosthesis 200 are implanted or positioned in one ear of the recipient, transducer 108 is positioned at the ear in which hearing prosthesis 100 and hearing prosthesis 200 are located, whereas transducer 208 is positioned at the other ear. Other positions of the transducers are possible in other embodiments as well.

Transducer 208 may be further configured to transmit to processor 204, via circuitry 203, a generated audio signal that is based on the detected sound waves. Depending on the desired configuration, transducer 208 may be one or more microphones, one or more telecoil induction pickup coils, or some other sound-detection device now known or later developed. For example, in embodiments in which hearing prosthesis 200 is an acoustic hearing aid, transducer 208 is configured to receive acoustic signals, and the processor 204 is configured to analyze and encode the acoustic signals into acoustic output signals for applying to a recipient's ear via a speaker or other output interface (not shown).

In embodiments in which hearing prosthesis 200 is a bone conduction device, transducer 208 is configured to receive acoustic signals, and processor 208 is configured to analyze and encode the acoustic signals into mechanical vibration output signals for applying to the bone anchored device recipient's skull via a mechanism to transmit sound via direct bone vibrations (not shown). In one particular example, hearing prosthesis 200 is a bone anchored device similar or identical to a Cochlear™ Baha® bone anchored device.

In embodiments in which the hearing prosthesis 200 is a direct acoustic cochlear implant, transducer 108 may be configured to analyze and encode acoustic signals into mechanical vibration output signals for applying to the direct acoustic cochlear implant recipient's inner ear via a mechanism to transmit sound via direct vibration (not shown). In addition, in embodiments in which the hearing prosthesis 200 is an auditory brain stem implant, transducer 108 is configured to analyze and encode acoustic signals into electrical stimulation output signals for applying to the auditory brain stem implant recipient's auditory nerve via one or more electrodes (not shown). Other types of devices with other types of configurations are possible in other embodiments as well.

Example Operation

In accordance with one embodiment generally, in an effort to deliver a higher quality signal to each hearing prosthesis in a binaural hearing prosthesis configuration, rather than immediately applying stimulation to the recipient in response to a received audio signal, each hearing prosthesis will first transmit its received audio signal to its processor (e.g., processor 104) as well as the other processor of the other hearing prosthesis (e.g., processor 204). Each processor will compare the audio signals to determine an audio signal that has a highest SNR. That processor will then cause the hearing prosthesis with which it is associated to apply stimulation in accordance with the determined highest-SNR audio signal. In other embodiments, other ways of delivering a higher SNR to each hearing prosthesis are possible as well.

Figure 3:
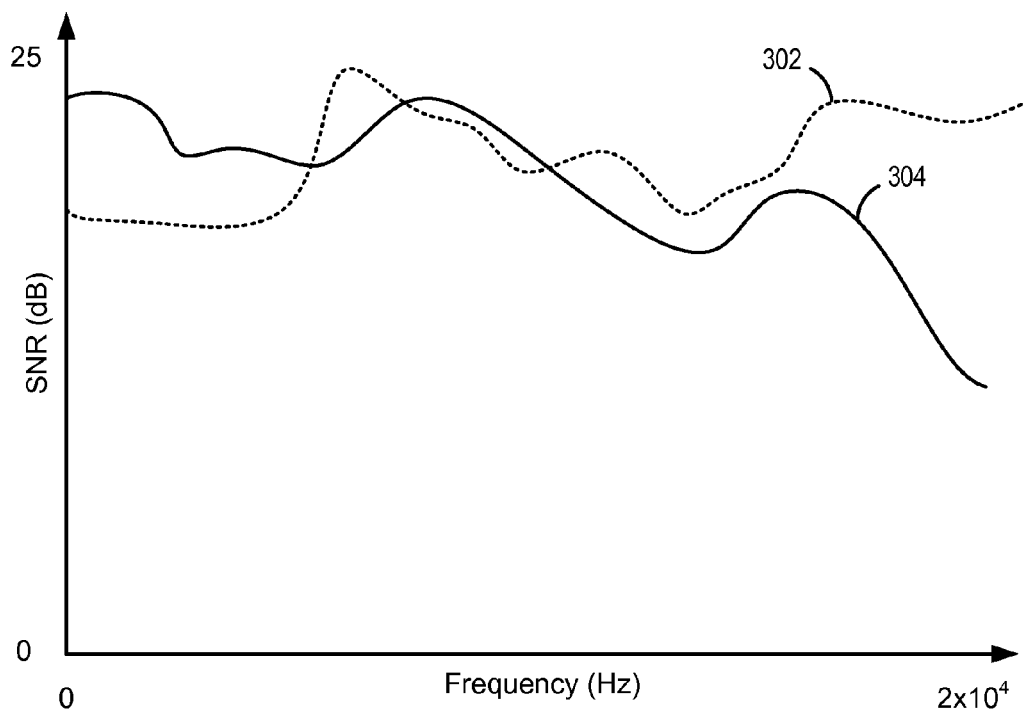
FIG. 3 is graph of signal to noise ratios for example signals according to some embodiments of the disclosed systems and methods.

To help illustrate the general process, reference will be made to SNRs of example audio signals. Accordingly, FIG. 3 depicts the SNR as a function of frequency for two example audio signals 302 and 304. In one embodiment, signal 302 represents the SNR of an audio signal received at transducer 208 of hearing prosthesis 200, whereas signal 304 represents the SNR of an audio signal received at transducer 108 of hearing prosthesis 100. As depicted in FIG. 3, signal 304 has a somewhat lower SNR toward the higher end of the frequency range than does signal 302. As described above, this may be the result of sound waves received at transducer 108 being attenuated by the recipient's head, or may be the result of some other phenomena.

In some embodiments, signals 302 and 304 represent the SNRs of audio signals that result from pre-processing. Non-limiting examples of such pre-processing include beamforming with directional microphones (or other spatial noise reduction), reducing feedback with notch filters, or other pre-processing that does not add/remove a frequency band based on an SNR determination.

Additionally, in some embodiments, the number of sources of audio signals exceeds two. In such embodiments, one or both of audio signals 302 or 204 are composites of signals collected from different sources (e.g. FM or other "wireless" microphones). Further, in some embodiments other audio signal measures are used instead of or in addition to SNR (e.g., input speech level).

In some embodiments, hearing prosthesis 200 transmits its received audio signal 302 to hearing prosthesis 100 (and more particularly, to processor 104 of command module 101) via data link 209. Upon receipt, hearing prosthesis 100 compares audio signal 302 and audio signal 304 to determine an audio signal with the highest SNR. Hearing prosthesis 100 can carry out this determination in a variety of ways. For example, in accordance with one example embodiment, hearing prosthesis 100 determines an audio signal with the highest SNR by calculating the average SNR of each audio signal over the entire frequency range and selecting the audio signal with the highest average SNR.

Figure 4:
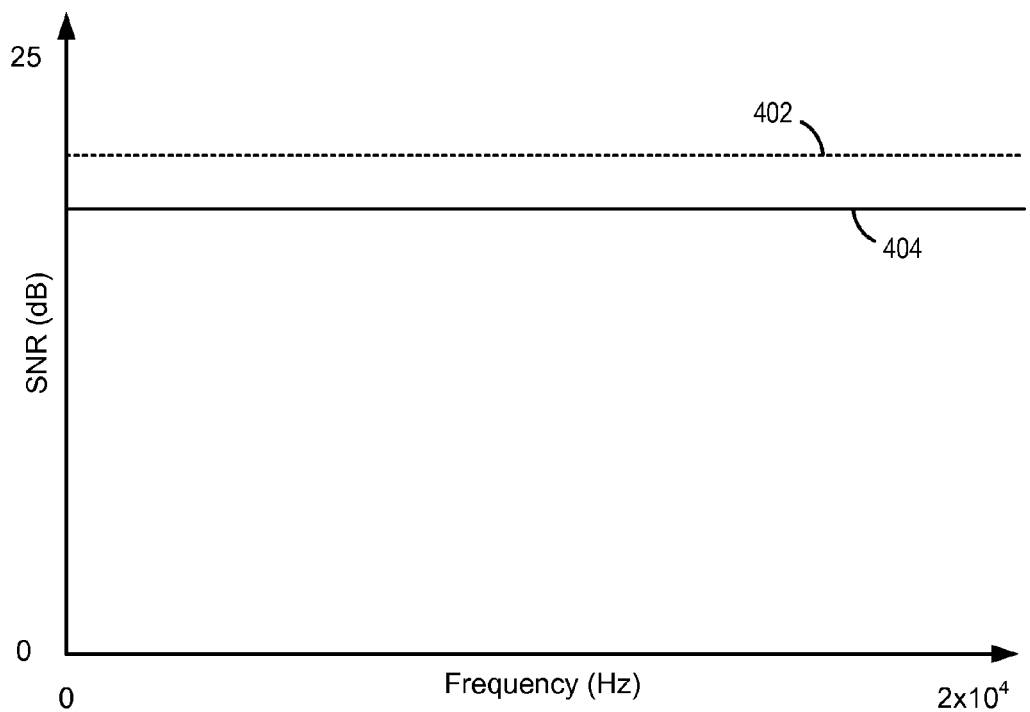
FIG. 4 is graph of signal to noise ratios for example signals according to some embodiments of the disclosed systems and methods.

FIG. 4 depicts the result of such an example calculation. More particularly, SNR 402 represents the average SNR of audio signal 302, whereas SNR 404 represents the average SNR of audio signal 304. As depicted in this example embodiment, SNR 402 is higher than SNR 404. As a result, hearing prosthesis 100 will use audio signal 302 (which was received at hearing prosthesis 200) instead of audio signal 304 (which was received at hearing prosthesis 100) in applying stimulation to the prosthesis recipient.

In some embodiments, and perhaps at the same time as hearing prosthesis 200 transmits its received audio signal 302 to hearing prosthesis 100, hearing prosthesis 100 transmits its received audio signal 304 to hearing prosthesis 200 (and more particularly, to processor 204 of hearing prosthesis 200) via data link 209. Upon receipt, hearing prosthesis 200 compares audio signal 304 and audio signal 302 to determine an audio signal with the highest SNR. Hearing prosthesis 200 can carry out this determination in any of the same ways as hearing prosthesis 100. And as a result of this determination, hearing prosthesis 200 will use the determined audio signal in applying stimulation to the prosthesis recipient.

In some embodiments, upon determining an audio signal with the highest SNR (such as audio signal 302 in the example embodiment depicted in FIGS. 3-4), hearing prosthesis 100 will divide the audio signal into two segments. One segment will constitute parts of the audio signal that are below a particular threshold frequency, and the other segment will constitute parts of the audio signal that are above the particular threshold frequency. In one particular embodiment, the threshold frequency is 500 Hz; however, in other embodiments, other threshold frequencies are used. Subsequently, hearing prosthesis 100 will use one of the two segments in applying stimulation to the prosthesis recipient and transmit the other of the two segments to hearing prosthesis 200. For example, in embodiments, in which hearing prosthesis 100 is a cochlear implant and hearing prosthesis 200 is an acoustic hearing aid, hearing prosthesis 100 will use the segment constituting parts of the audio signal that are above the particular threshold frequency, and transmit the other segment to hearing prosthesis 200. In other embodiments, the hearing prostheses will use other segments.

Preserving the provenance of one segment of the audio signal may improve the representation of "binaural" sound cues which can provide the recipient with the facility to localize the direction of sound sources. Choice of which segments and whether to preserve them may be determined in general such that the usefulness providing the higher SNR signal segments may be weighed against the need or benefit of providing binaural sound cues. For example, in some embodiments, hearing prosthesis 100 selects one or the other of preservation of "binaural" sound cues and the use of higher SNR signal segments as a result of environmental classification. In some embodiments favoring one or the other preservation of "binaural" sound cues and the use of higher SNR signal segments is a recipient option selected via a user interface of hearing prosthesis 100 (not shown). In such embodiments, a recipient is able to favor the latter while listening to a lecture or other speech in a noisy setting. In such situations, speech comprehension might be more important than preservation of "binaural" sound cues. In other situations, such as while walking in high traffic areas, preservation of "binaural" sound cues to avoid danger might be important than speech comprehension.

Individualization may be extended to the choice to enable or disable the use of higher SNR signal segments depending upon the recipient's hearing capacity for either ear. In some embodiments, such individualization is made through configuration of hearing prosthesis 100 to a recipient during a fitting session.

Figure 5:
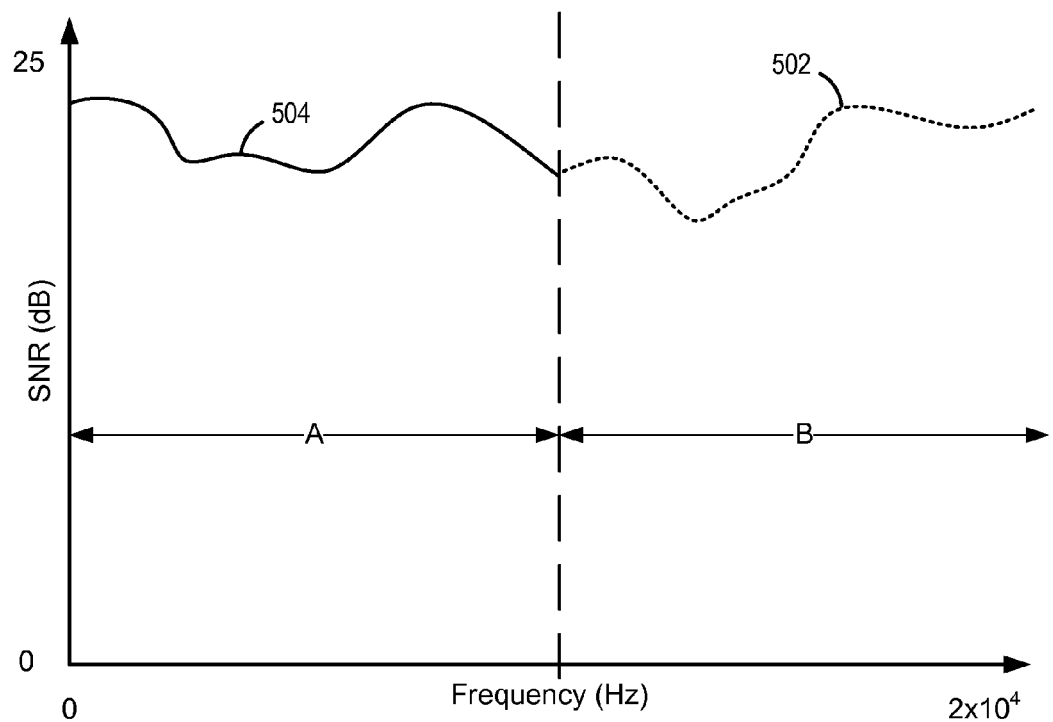
FIG. 5 is graph of a signal to noise ratio for an example signal according to some embodiments of the disclosed systems and methods.

In accordance with another embodiment, hearing prosthesis 100 determines an audio signal with the highest SNR by dividing the audio signals into separate frequency bands and determining which of the two audio signals has a higher SNR in each frequency band. Hearing prosthesis 100 will then construct a new audio signal from among the parts of each audio signal that have the highest SNR in each frequency band. FIG. 5 depicts one example of such a process. For example, FIG. 5 depicts two frequency bands, A and B. In this embodiment, hearing prosthesis 100 has determined that signal 304 has a higher average SNR than signal 302 in frequency band A, as depicted by signal part 504. And hearing prosthesis has determined that signal 302 has a higher average SNR than signal 304 in frequency band B, as depicted by signal part 502. As a result of these determinations, hearing prosthesis 100 constructs a new signal from signal parts 504 and 502 and uses this new signal in applying stimulation to the prosthesis recipient. Additionally, hearing prosthesis 100 transmits the new signal to hearing prosthesis 200 so that hearing prosthesis 200 can use the new signal in applying stimulation to the prosthesis recipient. Alternatively, hearing prosthesis 200 carries out the same determination and signal construction process as hearing prosthesis 100 and thereby constructs the same new signal as hearing prosthesis 100. Hearing prosthesis 200 will then apply stimulation to the prosthesis recipient in accordance with the new signal. Although frequency bands A and B are depicted in FIG. 5 as being about the same size and spanning about half of the audible frequency range, in practice, the two frequency bands may be of any size and may span some or all of the audible frequency range.

Figure 6:
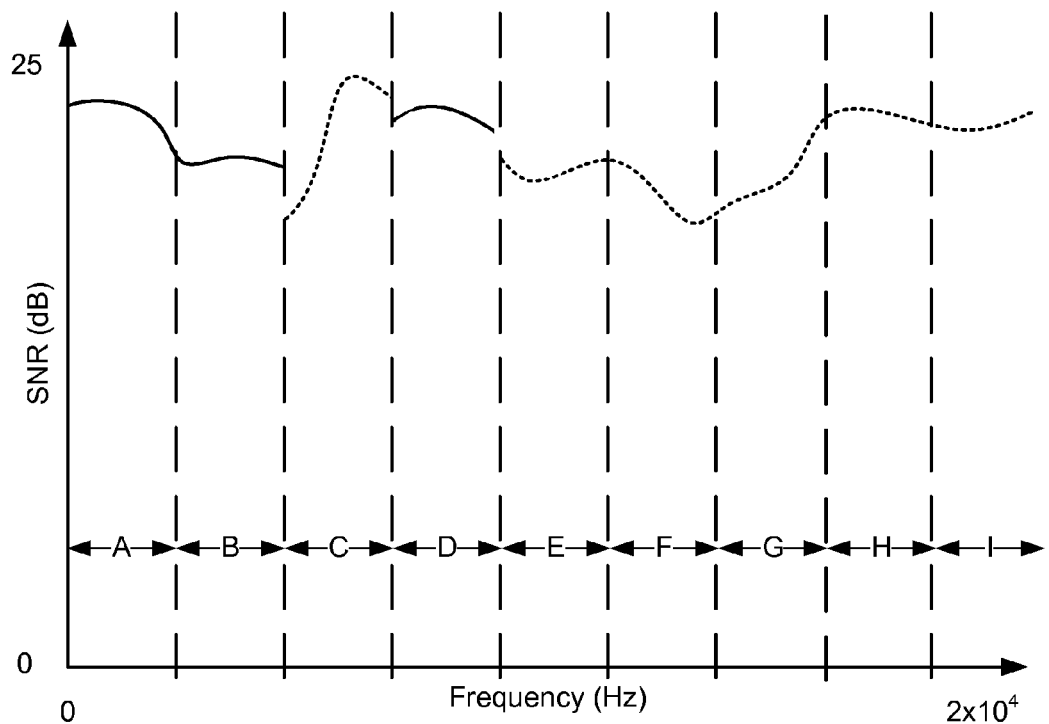
FIG. 6 is graph of a signal to noise ratio for an example signal according to some embodiments of the disclosed systems and methods.

FIG. 6 depicts another example of dividing the audio signals into separate frequency bands and determining which of the two audio signals has a higher SNR in each frequency band. For example, FIG. 6 depicts nine frequency bands, A-I. In this embodiment, hearing prosthesis 100 has determined that audio signal 304 has a higher average SNR than signal 302 in frequency bands A, B, and D. And hearing prosthesis 100 has determined that signal 302 has a higher average SNR than signal 304 in frequency bands C, E, F, G, H, and I. As a result of these determinations, hearing prosthesis 100 constructs a new signal from the individual signal parts depicted in FIG. 6 and uses this new signal in applying stimulation to the prosthesis recipient. Additionally, hearing prosthesis 100 transmits the new signal to hearing prosthesis 200 so that hearing prosthesis 200 can use the new signal in applying stimulation to the prosthesis recipient. Alternatively, hearing prosthesis 200 carries out the same determination and signal construction process as hearing prosthesis 100 and thereby constructs the same new signal as hearing prosthesis 100. Hearing prosthesis 200 will then apply stimulation to the prosthesis recipient in accordance with the new signal. Although FIG. 6 depicts nine frequency bands, each being roughly the same size, in practice, hearing prosthesis 100 may divide the audio signals into any number of frequency bands, each with roughly the same or perhaps different sizes.

In an alternative embodiment, rather than using the entirety of the new signal in applying stimulation to the prosthesis recipient at hearing prosthesis 100 and hearing prosthesis 200, hearing prosthesis 100 will, upon constructing the new signal, divide the new signal into two segments. One segment will constitute parts of the audio signal that are below a particular threshold frequency, and the other segment will constitute parts of the audio signal that are above the particular threshold frequency. In one particular embodiment, the threshold frequency is 500 Hz; however, in other embodiments, other threshold frequencies are used. Subsequently, hearing prosthesis 100 will use one of the two segments in applying stimulation to the prosthesis recipient and transmit the other of the two segments to hearing prosthesis 200. For example, in embodiments, in which hearing prosthesis 100 is a cochlear implant and hearing prosthesis 200 is an acoustic hearing aid, hearing prosthesis 100 will use the segment constituting parts of the audio signal that are above the particular threshold frequency, and transmit the other segment to hearing prosthesis 200. In other embodiments, the hearing prostheses will use other segments.

Figure 7:
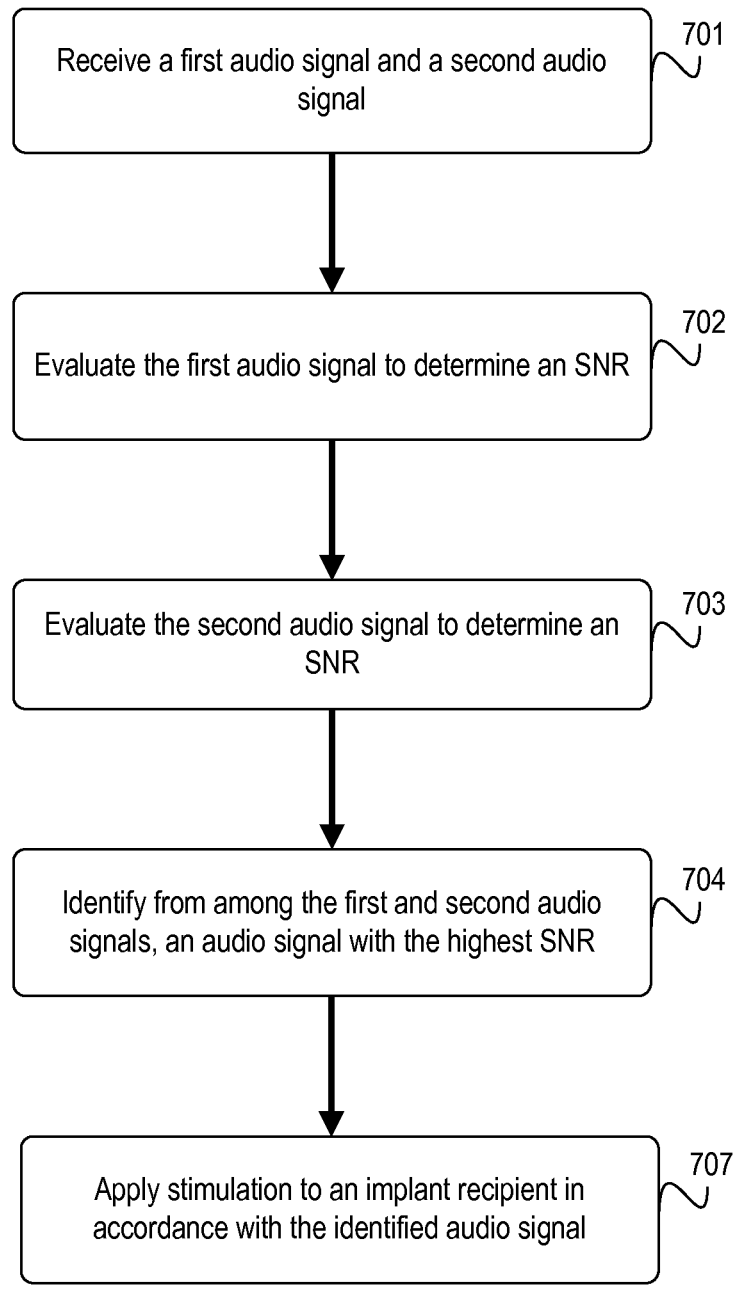
FIG. 7 is a flow chart depicting an example method, according to an example embodiment.

FIG. 7 is a flowchart depicting an example method for receiving and evaluating audio signals in a binaural hearing prosthesis configuration. The method depicted in FIG. 7 may be executed by one or more of the modules or sub-modules of hearing prosthesis 100 or hearing prosthesis 200, such as processor 104 or processor 204. As depicted, the method begins at block 701 where a processor (e.g., processor 104) receives a first audio signal and a second audio signal. In accordance with one embodiment, the first audio signal is output from transducer 108 of hearing prosthesis 100 as the result of sound waves received by transducer 108. And the second audio signal is output from transducer 208 of hearing prosthesis 200 as the result of sound waves received by transducer 208. In other embodiments, however, the first and second audio signals are received at other devices.

At blocks 702 and 703, the processor evaluates the first audio signal and the second audio signal to determine a respective SNR of each signal. In one embodiment, the processor determines the SNR of each signal as a function of frequency. However, the processor generally evaluates the signals according to known methods.

At block 704, the processor identifies from among the first and second signals, an audio signal with the highest SNR. According to one embodiment, the processor identifies an audio signal by selecting whichever of the first and second audio signals has the highest average SNR over all frequencies. According to another embodiment, the processor identifies an audio signal by first dividing each of the first and second audio signals into two or more frequency bands. Second, the processor evaluates the average SNR of the first and second signals in each frequency band. And third, the processor constructs a new audio signal from among parts of the first and second signal that have the highest SNR in each frequency band. Other ways of identifying an audio signal with the highest SNR are possible as well.

Finally, at block 707, the processor applies (or causes to be applied) stimulation to an implant recipient in accordance with the identified audio signal. For example, in one embodiment, hearing prosthesis 100 applies stimulation to a prosthesis recipient based on the identified signal (instead of the original signal output from transducer 108). And hearing prosthesis 200 applies stimulation to a prosthesis recipient based on the identified signal (instead of the original signal output from transducer 208). In another embodiment, and although not depicted, the processor of one hearing prosthesis transmits the identified audio signal to a processor of the other stimulation prosthesis so that the other hearing prosthesis can apply stimulation in accordance with the identified signal. Other examples are possible as well.

Figure 8:
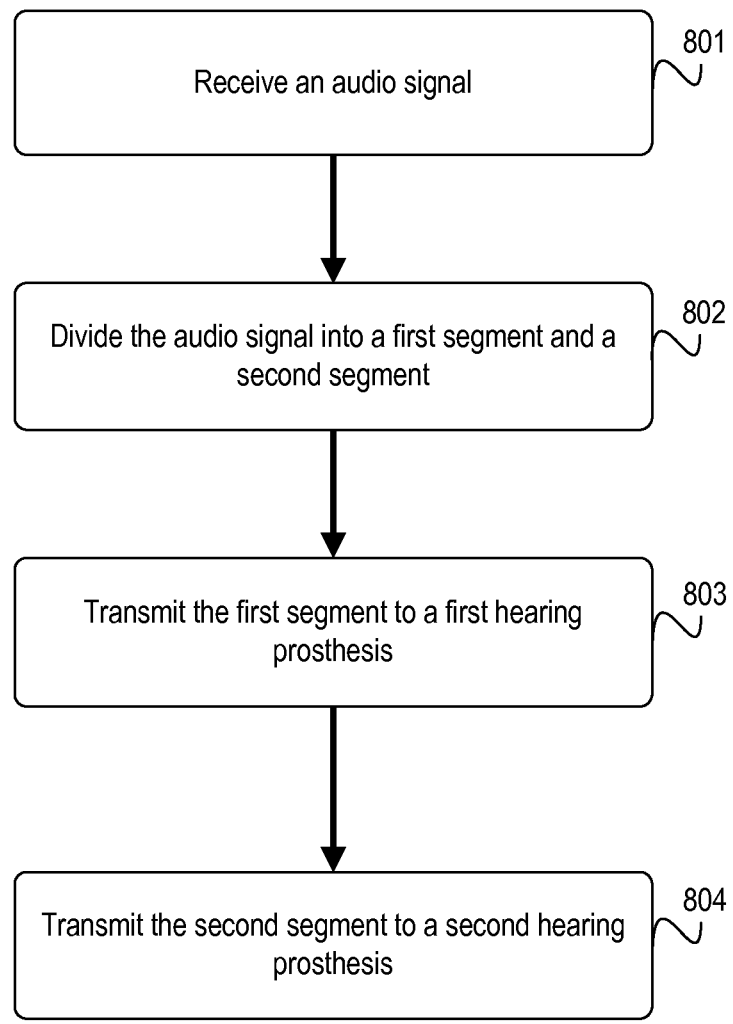
FIG. 8 is a flow chart depicting an example method, according to an example embodiment.

FIG. 8 is another flow chart depicting another example method for receiving and evaluating audio signals in a binaural prosthesis configuration. The method depicted in FIG. 8 may be executed by one or more of the modules or sub-modules of hearing prosthesis 100 or hearing prosthesis 200, such as processor 104 or processor 204. As depicted, the method begins at block 801 where a processor (e.g., processor 104) receives an audio signal. In accordance with one embodiment, the received audio signal is output from transducer 108 of hearing prosthesis 100 as the result of sound waves received by transducer 108. In accordance with another embodiment, the received signal is output from transducer 208 of hearing prosthesis 200 as the result of sound waves received by transducer 208. In accordance with still another embodiment, the received audio signal is the audio signal identified as a result of block 704 in the method depicted in FIG. 7. However, in other embodiments, the audio signal is received from other entities.

At block 802, the processor divides the audio signal into a first segment and a second segment. In some embodiments, the first segment is the part of the received audio signal that is above a particular threshold frequency, and the second segment is the part of the received audio signal that is below the particular threshold frequency. The threshold frequency can be any frequency, generally. In one example, the threshold frequency is 500 Hz.

At block 803, the processor transmits the first segment to a first hearing prosthesis. In one example, processor 104 transmits the first segment by causing the hearing prosthesis 100, generally (and stimulation module 111, particularly) to apply stimulation to a prosthesis recipient based on the first segment.

Finally, at block 804 the processor transmits the second segment to a second hearing prosthesis. In one example, processor 104 transmits (or causes to be transmitted) the second segment to hearing prosthesis 200. As a result, hearing prosthesis 200 applies stimulation to a prosthesis recipient based on the transmitted second segment (instead of, perhaps, an original signal output from transducer 208).

Computer Readable Media Implementations

In some embodiments, the disclosed features and functions of the systems, methods, and algorithms shown and described herein may be implemented as computer program instructions encoded on a computer readable media in a machine-readable format.

FIG. 9 depicts an example of an article of manufacture 900 including computer readable media with instructions for receiving and evaluating audio signals in a binaural hearing prosthesis configuration, according to some embodiments of the disclosed systems and methods. FIG. 9 shows a schematic illustrating a conceptual partial view of an example article of manufacture 900 that may include computer program instructions 902 for executing a computer process on a computing device, arranged according to at least some embodiments described herein.

In some examples, the article of manufacture 900 may include a non-transitory computer-readable medium 903, such as, but not limited to, a hard disk drive, a Compact Disc (CD), a Digital Video Disk (DVD), a digital tape, flash memory, etc. In some implementations, the article of manufacture 900 may include a non-transitory computer recordable medium 904, such as, but not limited to, a hard disk drive, a Compact Disc (CD), a Digital Video Disk (DVD), a digital tape, flash memory, etc.

The one or more programming instructions 902 may be, for example, computer executable and/or logic implemented instructions. In some embodiments, processor 104 of hearing prosthesis 100 or processor 204 of hearing prosthesis 200, alone or in combination with one or more other processors associated with the hearing prostheses 100 and 200, may be configured to perform various operations, functions, or actions to implement the features and functionality of the disclosed systems and methods based at least in part on the programming instructions 902.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
receiving a first audio signal from a first transducer;
receiving a second audio signal from a second transducer;
evaluating the first audio signal and determining thereby a first audio signal measure;
evaluating the second audio signal and determining thereby a second audio signal measure;
based on the evaluating, identifying from among the first audio signal and the second audio signal a particular audio signal that has a certain quality with respect to the audio signal measures; and
applying stimulation to an implant recipient in accordance with the identified audio signal, wherein (i) the first audio signal measure is a first signal-to-noise ratio (SNR), (ii) the second audio signal measure is a second SNR, and (iii) the certain quality with respect to the audio signal measures is a highest SNR.

2. The method of claim 1,
wherein the first transducer is associated with a first hearing prosthesis and the second transducer is associated with a second hearing prosthesis, and
wherein applying stimulation to an implant recipient in accordance with the identified audio signal comprises (i) applying stimulation at the first hearing prosthesis in accordance with the identified audio signal, and (ii) applying stimulation at the second hearing prosthesis in accordance with the identified audio signal.

3. The method of claim 1, wherein the first transducer is located on one side of an implant recipient's head, and wherein the second transducer is located on another side of the implant recipient's head.

4. A method comprising:
receiving a first audio signal from a first transducer;
receiving a second audio signal from a second transducer;
evaluating the first audio signal and determining thereby a first audio signal measure;
evaluating the second audio signal and determining thereby a second audio signal measure;
based on the evaluating, identifying from among the first audio signal and the second audio signal a particular audio signal that has a certain quality with respect to the audio signal measures; and
applying stimulation to an implant recipient in accordance with the identified audio signal, wherein:
(i) the first audio signal comprises a first set of component signals that correspond to a set of frequency bands,
(ii) the second audio signal comprises a second set of component signals that correspond to the set of frequency bands, the first set of component signals and the second set of component signals collectively comprising a plurality of component signals,
(iii) evaluating the first audio signal comprises, for each individual component signal of the first set of component signals, determining a respective audio signal measure of the individual component signal, and
(iv) evaluating the second audio signal comprises, for each individual component signal of the second set of component signals, determining a respective audio signal measure of the individual component signal.

5. The method of claim 4, wherein identifying from among the first audio signal and the second audio signal a particular audio signal that has a certain quality with respect to the audio signal measures comprises:
constructing a third audio signal using a subset of the plurality of component signals, each individual component signal corresponding to a particular frequency band and having a certain quality with respect to the audio signal measures from among the component signals that correspond to that particular frequency band.

6. A method comprising:
receiving an audio signal from a transducer;
dividing the audio signal into a first segment and a second segment, the first segment comprising parts of the audio signal that are in frequency bands of greater magnitude than a threshold frequency, and the second segment comprising parts of the audio signal that are in frequency bands of smaller magnitude than the threshold frequency;
transmitting the first segment to a first hearing prosthesis; and
transmitting the second segment to a second hearing prosthesis.

7. The method of claim 6, wherein the first hearing prosthesis is a cochlear implant, and wherein the second hearing prosthesis is not a cochlear implant.

8. The method of claim 6, further comprising:
applying electrical stimulation to an implant recipient, the electrical stimulation being applied in accordance with the first segment of the audio signal; and
applying acoustic stimulation to the implant recipient, the acoustic stimulation being applied in accordance with the second segment of the audio signal.

9. The method of claim 6,
wherein receiving an audio signal from a transducer comprises receiving a first audio signal from a first transducer and receiving a second audio signal from a second transducer, and wherein dividing the audio signal into a first segment and a second segment comprises:
(i) dividing the first audio signal into a respective first sub-portion and a respective second sub-portion, the respective first sub-portion including parts of the first audio signal that are in frequency bands of greater magnitude than the threshold frequency and the respective second sub-portion including parts of the first audio signal that are in frequency bands of greater magnitude than the threshold frequency,
(ii) dividing the second audio signal into a respective first sub-portion and a respective second sub-portion, the respective first sub-portion including parts of the second audio signal that are in frequency bands of greater magnitude than the threshold frequency and the respective second sub-portion including parts of the second audio signal that are in frequency bands of greater magnitude than the threshold frequency,
(iii) evaluating an audio signal measure of each respective sub-portion of the first audio signal, and evaluating an audio signal measure of each respective sub-portion of the second audio signal, and
(iv) based on the evaluating, determining as the first segment, a respective first sub-portion that has a certain quality with respect to the audio signal measures from among the respective first sub-portions, and determining as the second segment, a respective second sup-portion that has a certain quality with respect to the audio signal measures from among the respective second sub-portions.

10. The method of claim 9, wherein the first transducer is located on one side of an implant recipient's head, and wherein the second transducer is located on another side of the implant recipient's head.

11. The method of claim 6, wherein receiving an audio signal from a transducer comprises:
receiving a first audio signal from a first transducer and receiving a second audio signal from a second transducer, the first audio signal comprising a first set of component signals that correspond to a set of frequency bands, and the second audio signal comprising a second set of component signals that correspond to the set of frequency bands, the first set of component signals and the second set of component signals collectively comprising a plurality of component signals,
for each individual component signal of the first set of component signals, determining a respective audio signal measure of the individual component signal;
for each individual component signal of the second set of component signals, determining a respective audio signal measure of the individual component signal; and
constructing a third audio signal using a subset of the plurality of component signals, each individual component signal corresponding to a particular frequency band and having a certain quality with respect to the audio signal measures from among the component signals that correspond to that particular frequency band.

12. The method of claim 11,
wherein dividing the audio signal into the first segment and the second segment comprises dividing the third audio signal into a first segment and a second segment, the first segment of the third audio signal comprising parts of the third audio signal that are in frequency bands of greater magnitude than the threshold frequency, and the second segment of the third audio signal comprising parts of the third audio signal that are in frequency bands of smaller magnitude than the threshold frequency.

13. The method of claim 12,
wherein the first transducer is one side of an implant recipient's head and is communicatively coupled with the first hearing prosthesis, the first hearing prosthesis being a cochlear implant,
wherein the second transducer is located on another side of the implant recipient's head and is communicatively coupled with the second hearing prosthesis, the second hearing prosthesis being an acoustic device, and
wherein the method further comprises the cochlear implant applying to the implant recipient electrical stimulation in accordance with the first segment of the third audio signal, and the acoustic device applying to the implant recipient acoustic stimulation in accordance with the second segment of the third audio signal.

14. A system comprising:
a first stimulation prosthesis;
a second stimulation prosthesis; and
coupled to at least one of the first stimulation prosthesis and the second stimulation prosthesis, one or more processors configured for (i) receiving a first signal via a first receiver, (ii) receiving a second signal via a second receiver, (iii) determining an audio signal measure of the first signal and determining an audio signal measure of the second signal, (iv) identifying from among the first signal and the second signal a particular signal that has a certain quality with respect to the audio signal measures, and (v) causing one or both of the first stimulation prosthesis and the second stimulation prosthesis to apply stimulation to an implant recipient in accordance with at least part of the identified signal wherein:
(a) the first signal is a first audio signal, the second signal is a second audio signal, and the identified signal is an identified audio signal, and
(b) causing one or both of the first stimulation prosthesis and the second stimulation prosthesis to apply stimulation comprises (1) dividing the identified signal into a first segment and a second segment, the first segment comprising parts of the audio signal that are in frequency bands of greater magnitude than a threshold frequency, and the second segment comprising parts of the audio signal that are in frequency bands of smaller magnitude than the threshold frequency, and (2) causing the first stimulation prosthesis to apply stimulation in accordance with the first segment and causing the second stimulation prosthesis to apply stimulation in accordance with the second segment.

15. The system of claim 14, wherein the first receiver is a first transducer located on one side of a prosthesis recipient's head, and wherein the second receiver is a second transducer located on another side of the prosthesis recipient's head.

16. The system of claim 14, wherein the one or more processors are further configured for receiving the second signal at the second stimulation prosthesis and transmitting the second signal to the first stimulation prosthesis.

17. A system comprising:
a first stimulation prosthesis;
a second stimulation prosthesis; and
coupled to at least one of the first stimulation prosthesis and the second stimulation prosthesis, one or more processors configured for (i) receiving a first signal via a first receiver, (ii) receiving a second signal via a second receiver, (iii) determining an audio signal measure of the first signal and determining an audio signal measure of the second signal, (iv) identifying from among the first signal and the second signal a particular signal that has a certain quality with respect to the audio signal measures, and (v) causing one or both of the first stimulation prosthesis and the second stimulation prosthesis to apply stimulation to an implant recipient in accordance with at least part of the identified signal, wherein:
(a) the first signal is a first audio signal, the second signal is a second audio signal, and the identified signal is an identified audio signal,
(b) the first audio signal comprises a first set of component signals that correspond to a set of frequency bands,
(c) the second audio signal comprises a second set of component signals that correspond to the set of frequency bands, the first set of component signals and the second set of component signals collectively comprising a plurality of component signals,
(d) determining an audio signal measure of the first audio signal comprises, for each individual component signal of the first set of component signals, determining a respective audio signal measure of the individual component signal, and
(e) determining an audio signal measure of the second audio signal comprises, for each individual component signal of the second set of component signals, determining a respective audio signal measure of the individual component signal.

18. The system of claim 17, wherein identifying from among the first signal and the second signal a particular signal that has a certain quality with respect to the audio signal measures comprises constructing a third audio signal using a subset of the plurality of component signals, each individual component signal corresponding to a particular frequency band and having a certain quality with respect to the audio signal measures from among the component signals that correspond to that particular frequency band.

19. The system of claim 18,
wherein causing one or both of the first stimulation prosthesis and the second stimulation prosthesis to apply stimulation comprises (a) dividing the identified signal into a first segment and a second segment, the first segment comprising parts of the audio signal that are in frequency bands of greater magnitude than a threshold frequency, and the second segment comprising parts of the audio signal that are in frequency bands of smaller magnitude than the threshold frequency, and (b) causing the first stimulation prosthesis to apply stimulation in accordance with the first segment and causing the second stimulation prosthesis to apply stimulation in accordance with the second segment.

\* \* \* \* \*